(12) United States Patent
Ono

(10) Patent No.: US 10,266,642 B2
(45) Date of Patent: Apr. 23, 2019

(54) CRYSTAL POLYMORPHISM OF INCLUSION COMPOUND AND METHOD FOR PRODUCING SAME, AND CURABLE RESIN COMPOSITION

(71) Applicant: NIPPON SODA CO., LTD., Tokyo (JP)

(72) Inventor: Kazuo Ono, Ichihara (JP)

(73) Assignee: NIPPON SODA CO., LTD., Tokyo (JP)

( * ) Notice: Subject to any disclaimer, the term of this patent is extended or adjusted under 35 U.S.C. 154(b) by 34 days.

(21) Appl. No.: 15/504,112

(22) PCT Filed: Aug. 27, 2015

(86) PCT No.: PCT/JP2015/004313
§ 371 (c)(1),
(2) Date: Feb. 15, 2017

(87) PCT Pub. No.: WO2016/038827
PCT Pub. Date: Mar. 17, 2016

(65) Prior Publication Data
US 2017/0267810 A1 Sep. 21, 2017

(30) Foreign Application Priority Data

Sep. 8, 2014 (JP) .................. 2014-181844
Jan. 9, 2015 (JP) .................. 2015-003573

(51) Int. Cl.
*C08G 59/62* (2006.01)
*C07C 37/84* (2006.01)
(Continued)

(52) U.S. Cl.
CPC ............ *C08G 59/621* (2013.01); *C07C 37/84* (2013.01); *C07C 39/15* (2013.01); *C07D 233/64* (2013.01);
(Continued)

(58) Field of Classification Search
CPC ...... C08G 59/621; C08G 59/40; C08G 59/62; C08G 59/56; C08G 59/5073; C07C 37/84; C07C 39/15; C07D 233/64; C07B 2200/13
(Continued)

(56) References Cited

U.S. PATENT DOCUMENTS

2004/0030123 A1  2/2004  Amaike et al.
2010/0022744 A1  1/2010  Kaneko et al.
(Continued)

FOREIGN PATENT DOCUMENTS

CN    102341430 A    2/2012
CN    102574988 A    7/2012
(Continued)

OTHER PUBLICATIONS

Mar. 23, 2017 International Preliminary Report on Patentability issued in International Patent Application No. PCT/JP2015/004313.
(Continued)

*Primary Examiner* — David T Karst
(74) *Attorney, Agent, or Firm* — Oliff PLC

(57) ABSTRACT

It is to provide a more stable crystal polymorph of a clathrate compound consisting of 1,1,2,2-tetrakis(4-hydroxyphenyl)ethane and 2-phenyl-4-methyl-5-hydroxymethylimidazole (molar ratio 1:2). A novel crystal polymorph of a clathrate compound, consisting of 1,1,2,2-tetrakis(4-hydroxyphenyl)ethane and 2-phenyl-4-methyl-5-hydroxymethylimidazole (molar ratio 1:2) and has diffraction peaks at diffraction angles (2θ) of 11.20°, 13.36°, 14.36°, 18.16°, 19.20°, 19.68°, 20.84°, 21.48°, 22.56°, 23.76° and 24.08° in a powder X-ray diffraction pattern as measured using a CuKα ray, can be obtained by, for example, further recrystallizing a crystal obtained by a conventionally known method or the like.

5 Claims, 8 Drawing Sheets

(51) Int. Cl.
  *C07C 39/15* (2006.01)
  *C07D 233/64* (2006.01)
  *C08G 59/40* (2006.01)
  *C08G 59/56* (2006.01)
  *C08G 59/50* (2006.01)

(52) U.S. Cl.
  CPC ......... *C08G 59/40* (2013.01); *C08G 59/5073* (2013.01); *C08G 59/56* (2013.01); *C08G 59/62* (2013.01); *C07B 2200/13* (2013.01)

(58) Field of Classification Search
  USPC ....................................................... 525/526
  See application file for complete search history.

(56) References Cited

U.S. PATENT DOCUMENTS

| | | | |
|---|---|---|---|
| 2012/0004349 A1 | 1/2012 | Kaneko et al. | |
| 2012/0004377 A1* | 1/2012 | Kaneko | C07D 233/54 525/533 |
| 2012/0196991 A1 | 8/2012 | Ono et al. | |

FOREIGN PATENT DOCUMENTS

| | | |
|---|---|---|
| EP | 0949286 A1 | 10/1999 |
| EP | 2 617 750 A1 | 7/2013 |
| EP | 3 248 965 A1 | 11/2017 |
| JP | H11-071449 A | 3/1999 |
| JP | 2002-179597 A | 6/2002 |
| JP | 2002-316953 A | 10/2002 |
| JP | 2007-191450 A | 8/2007 |
| JP | 2010-241872 A | 10/2010 |
| WO | 2005/082823 A1 | 9/2005 |
| WO | 2008075427 A1 | 6/2008 |

OTHER PUBLICATIONS

Amanokura et al., "Curing Behavior of Epoxy Resin Initiated by Amine-Containing Inclusion Complexes," Polymer Journal, 2007, 39(8), 845-852.

Feb. 16, 2018 extended European Search Report issued in European Patent Application No. 15839387.6.

* cited by examiner

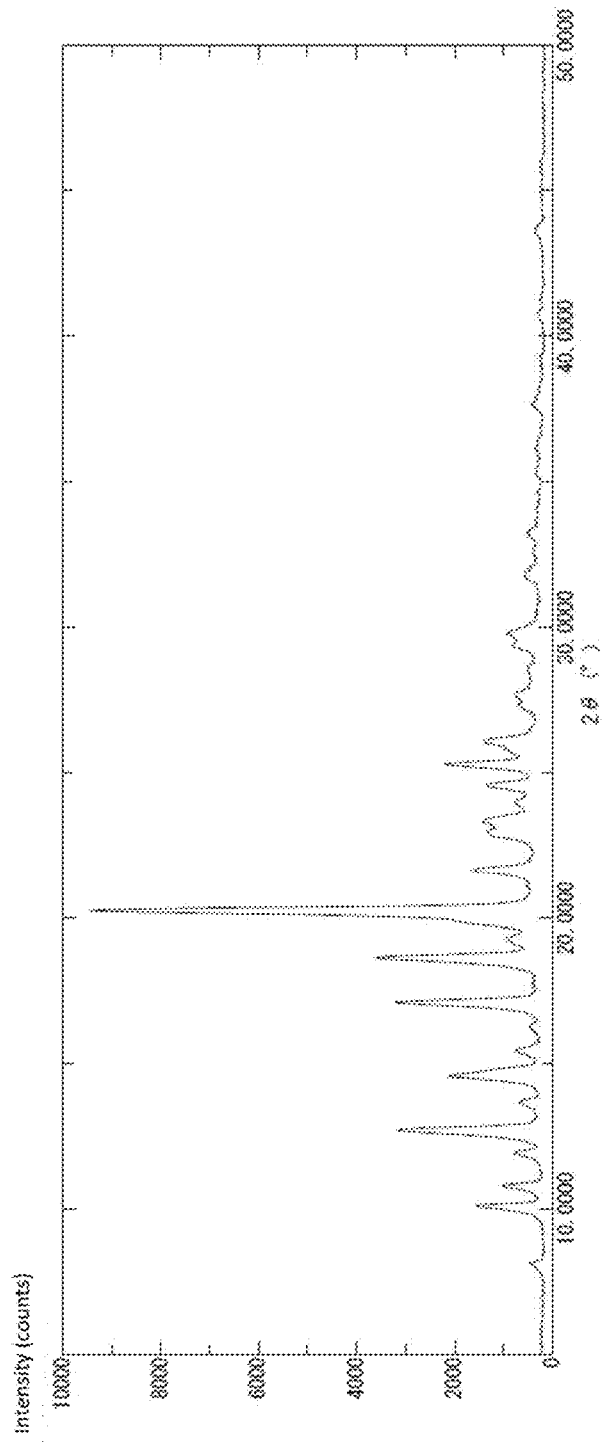
[Figure 1]

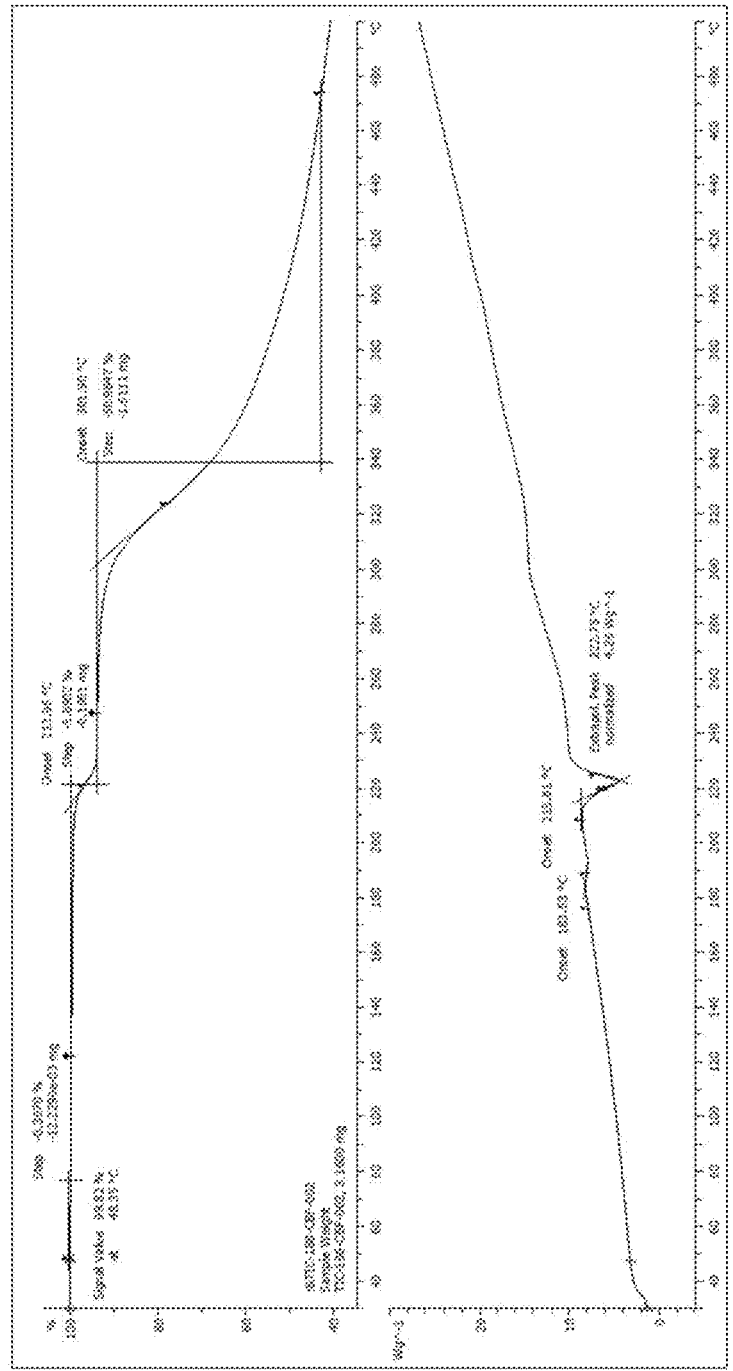
[Figure 2]

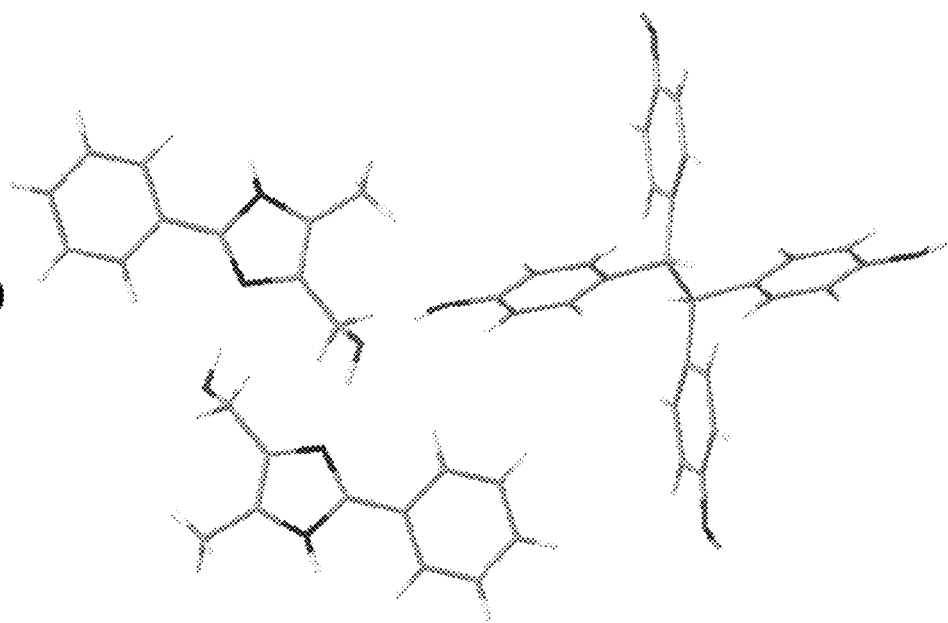
[Figure 3]

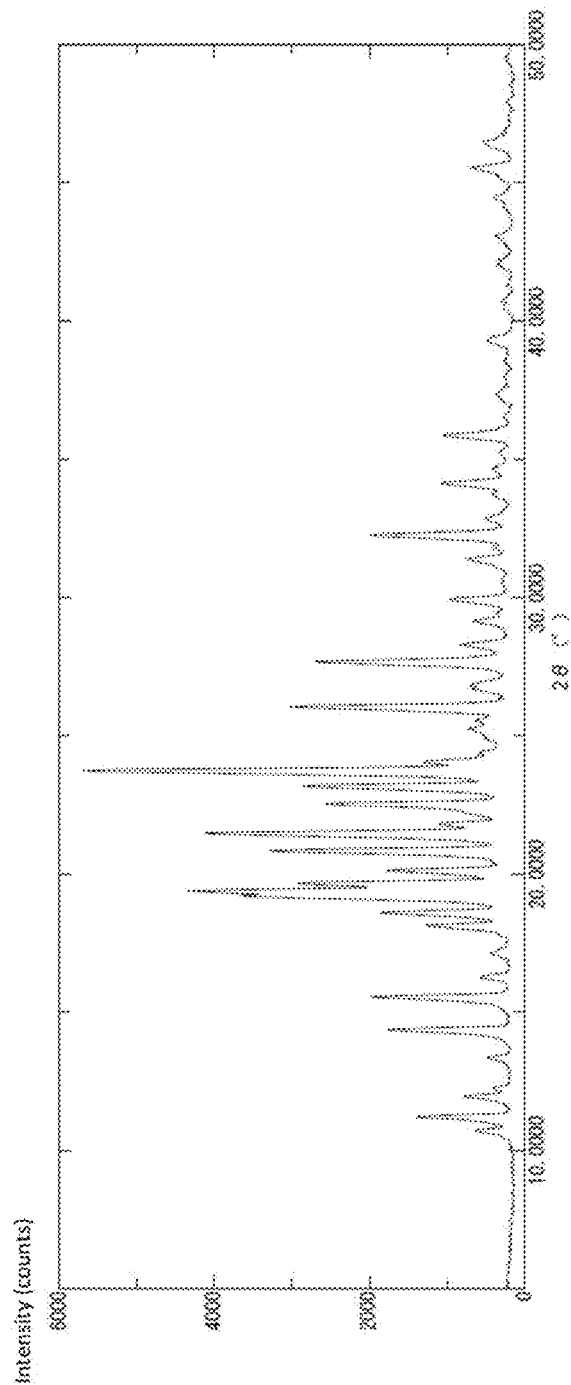
[Figure 4]

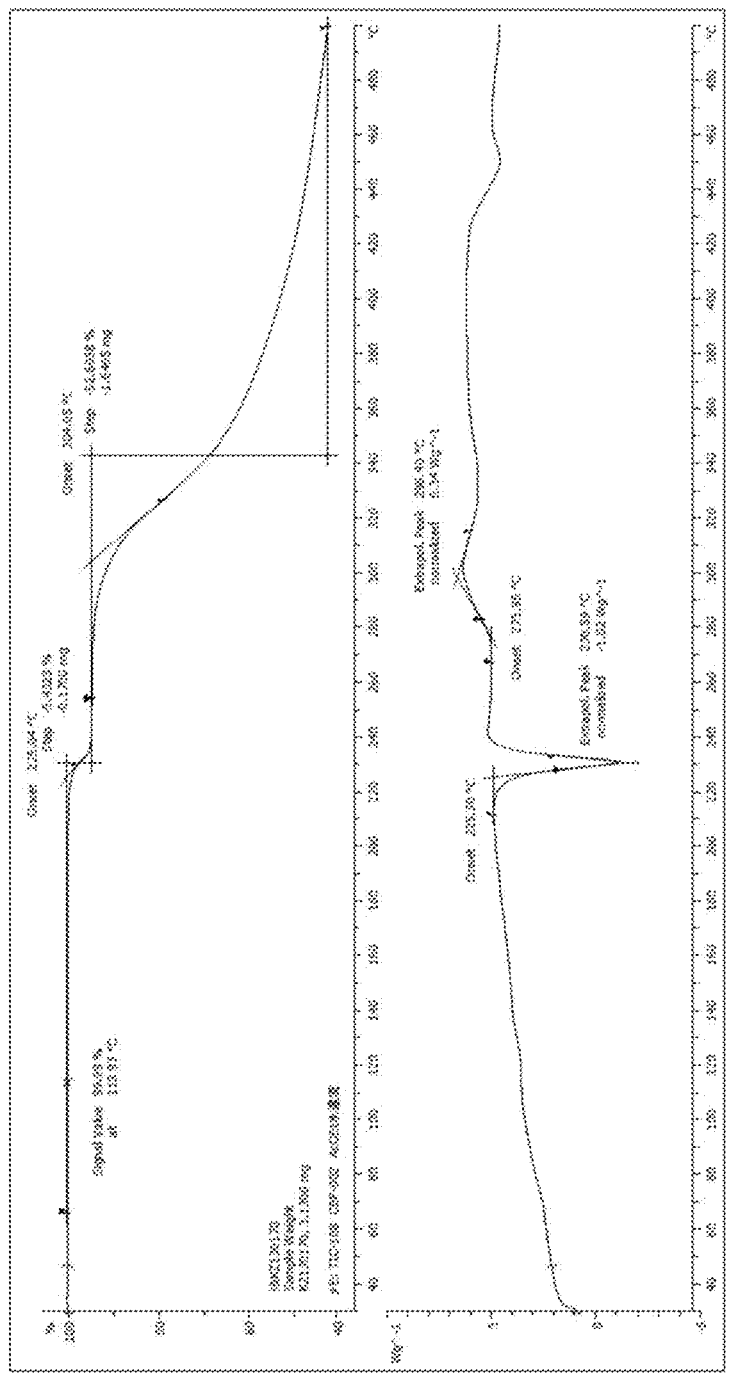
[Figure 5]

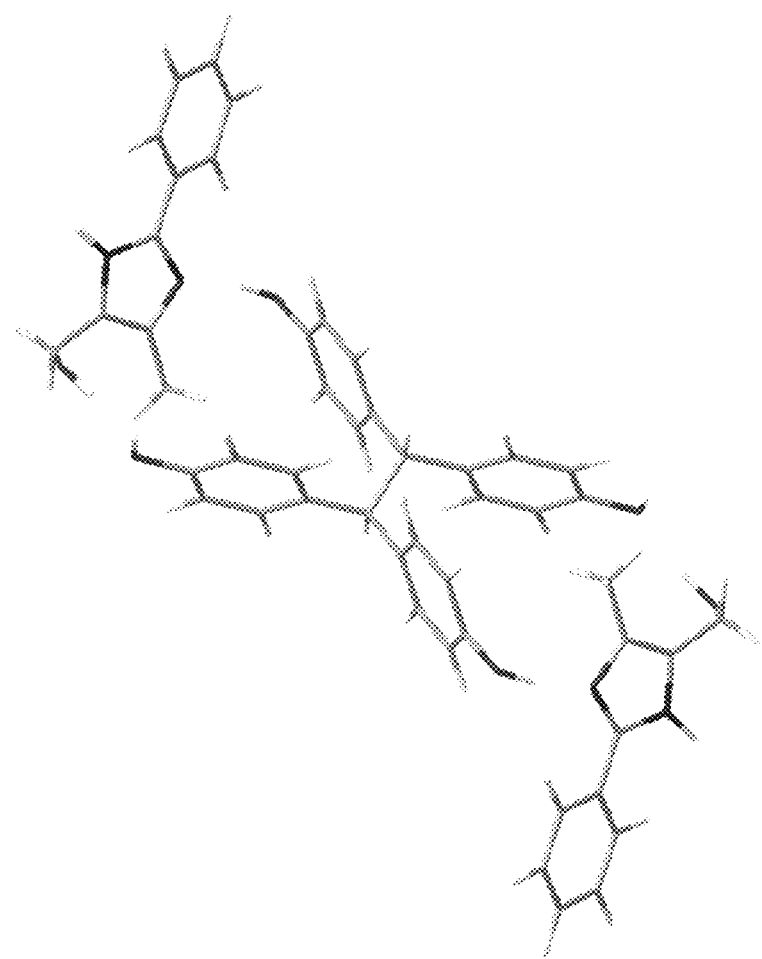
[Figure 6]

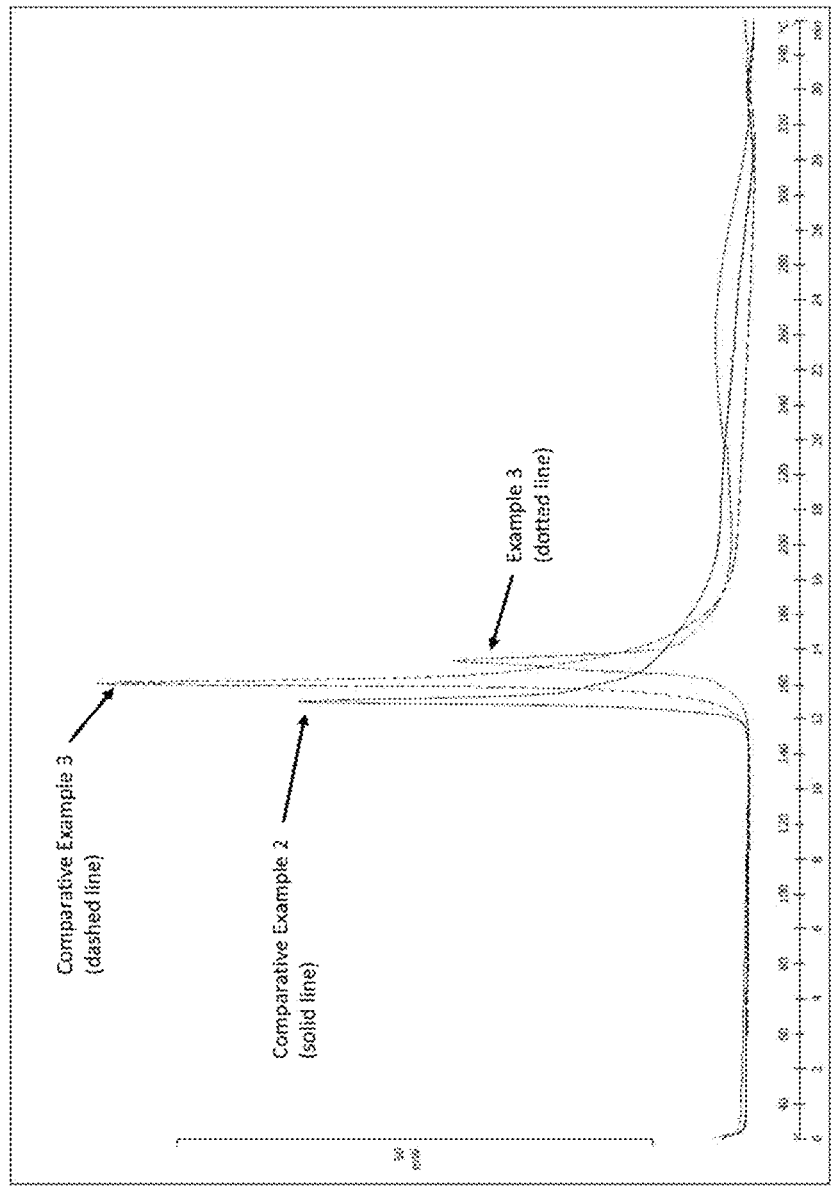

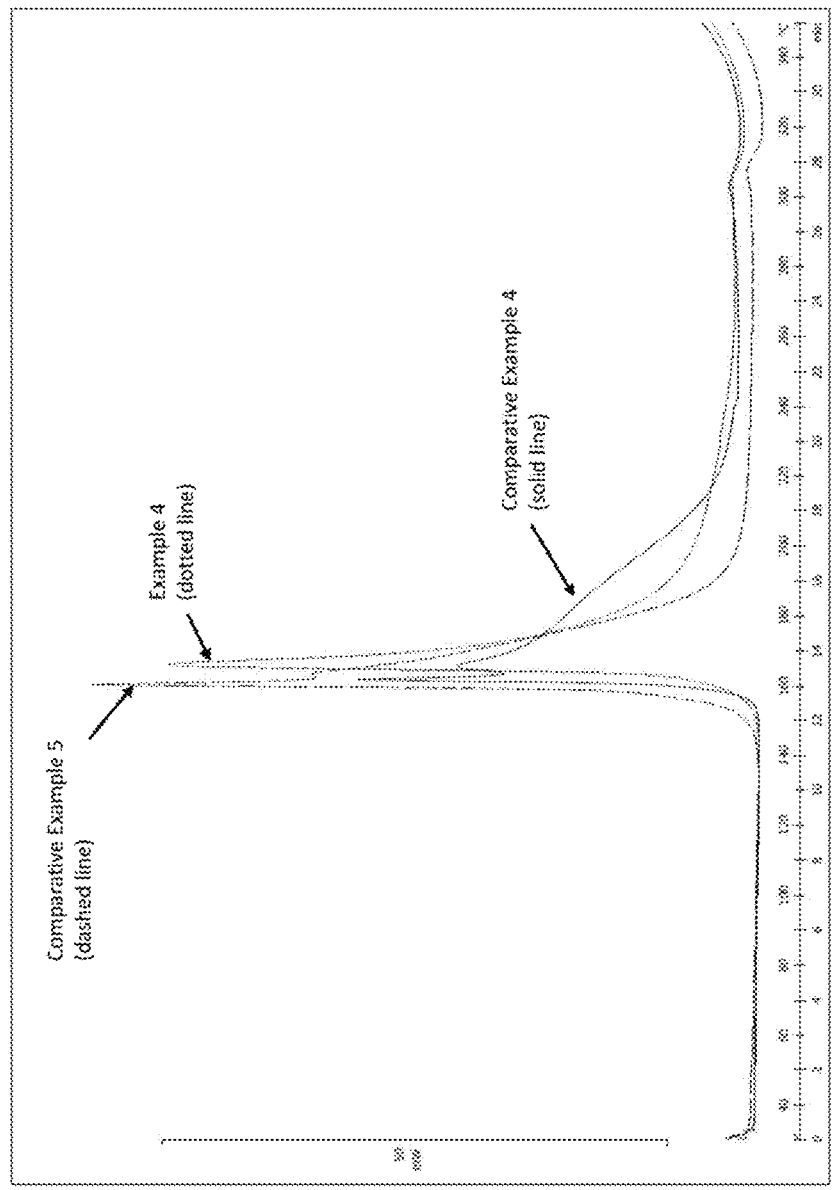
[Figure 8]

CRYSTAL POLYMORPHISM OF INCLUSION COMPOUND AND METHOD FOR PRODUCING SAME, AND CURABLE RESIN COMPOSITION

TECHNICAL FIELD

The present invention relates to a novel crystal polymorph of a clathrate compound consisting of 1,1,2,2-tetrakis(4-hydroxyphenyl)ethane (hereinafter sometimes abbreviated to TEP) and 2-phenyl-4-methyl-5-hydroxymethylimidazole (hereinafter sometimes abbreviated to 2P4MHZ) and method of producing the same, and a curable resin composition. The present application claims priority to Japanese Patent Application No. 2014-181844 filed on Sep. 8, 2014 and Japanese Patent Application No. 2015-003573 filed on Jan. 9, 2015, the contents of which are incorporated herein by reference.

BACKGROUND ART

It is conventionally known that tetrakisphenols and imidazole form a clathrate compound and it is also known that those exert their superior potentiality as a curing agent or a curing accelerator for epoxy resins.

For example, Patent Document 1 describes a curing agent for epoxy resins, characterized in that the agent consists of a clathrate of a tetrakisphenol-based compound and a compound that cures epoxy resin by reacting with epoxy group. TEP and 2P4MHZ are exemplified as a tetrakisphenol-based compound and a compound that cures epoxy resins by reacting with epoxy group, respectively.

Patent Document 2 describes that when TEP and 2P4MHZ are suspended in ethyl acetate, heated under reflux for 3 hours, and then cooled to room temperature, crystals of a clathrate compound can be obtained.

Further, Patent Document 3 describes a method of producing a clathrate compound, comprising preparing the compound by dispersing a solid host compound triturated in advance to an average particle diameter of less than or equal to 1.6 μm and a solid or liquid guest compound into a poor solvent of a solid host compound and a solid or liquid guest compound and keeping the temperature more than or equal to 50° C. and less than or equal to the release temperature of the guest compound, and water is exemplified as a poor solvent.

PRIOR ART DOCUMENTS

Patent Documents

Patent Document 1: Japanese unexamined Patent Application Publication No. 11-071449
Patent Document 2: Japanese unexamined Patent Application Publication No. 2007-191450
Patent Document 3: Japanese unexamined Patent Application Publication No. 2002-316953

SUMMARY OF THE INVENTION

Object to be Solved by the Invention

Crystals of any clathrate compound obtained by the above-described methods are a crystal (hereinafter sometimes abbreviated to crystal A) that has characteristic diffraction peaks at diffraction angles (2θ) of 8.12°, 10.12°, 12.72°, 13.68°, 14.60° and 20.24° in a powder X-ray diffraction pattern, and other crystal polymorph had not been known. Further, crystal A obtained in a conventional manner was sometimes not able to fully exert the effect expected as a clathrate compound depending on the kinds of epoxy resin being used.

The object of the present invention is to provide a new crystal polymorph that can exert an effect as a clathrate compound regardless of the type of epoxy resin.

Means to Solve the Object

The present inventors have diligently studied to solve the above-described object and resulted in finding that a novel crystal polymorph can be obtained by recrystallizing the crystal A or crystallizing after dissolving TEP and 2P4MHZ in a solvent and that the crystal stably exerts its effect as a clathrate compound regardless of the type of epoxy resin, and thus completed the present invention.

The present invention, specifically, relates to:

(1) a crystal polymorph of a clathrate compound consisting of 1,1,2,2-tetrakis(4-hydroxyphenyl)ethane and 2-phenyl-4-methyl-5-hydroxymethylimidazole (molar ratio 1:2), wherein the crystal polymorph has diffraction peaks at diffraction angles (2θ) of 11.20°, 13.36°, 14.36°, 18.16°, 19.20°, 19.68°, 20.84°, 21.48°, 22.56°, 23.76° and 24.08° in a powder X-ray diffraction pattern as measured using a CuKα ray.

The present invention further relates to:

(2) a method of producing the crystal polymorph according to (1), comprising a step of recrystallizing a crystal of a clathrate compound consisting of 1,1,2,2-tetrakis(4-hydroxyphenyl)ethane and 2-phenyl-4-methyl-5-hydroxymethylimidazole, wherein the crystal has diffraction peaks at diffraction angles (2θ) of 8.12°, 10.12°, 12.72°, 13.68°, 14.60° and 20.24° in a powder X-ray diffraction pattern as measured using a CuKα ray, and (3) a method of producing the crystal polymorph according to (1), comprising a step of crystallizing a clathrate compound consisting of 1,1,2,2-tetrakis(4-hydroxyphenyl)ethane and 2-phenyl-4-methyl-5-hydroxymethylimidazole from an alcohol solution or suspension containing 1,1,2,2-tetrakis(4-hydroxyphenyl)ethane and 2-phenyl-4-methyl-5-hydroxymethylimidazole.

The present invention further relates to:

(4) a curing agent for epoxy resins or a curing accelerator for epoxy resins, containing the crystal polymorph according to (1), and (5) a curable resin composition containing an epoxy resin and the curing agent for epoxy resins or the curing accelerator for epoxy resins according to (4), or a cured product thereof.

Effects of Invention

The crystal of the clathrate compound consisting of TEP and 2P4MHZ of the present invention is a novel crystal polymorph, having a good preservation stability as a composition by mixing with epoxy resins as compared to conventionally known crystal A, showing superior curing characteristics as a curing agent or a curing accelerator for epoxy resins, and also showing stable characteristics as a clathrate compound regardless of the type of epoxy resin.

BRIEF DESCRIPTION OF DRAWINGS

FIG. 1 shows powder X-ray diffraction (XRD) of the crystal (crystal A) obtained in Comparative Example 1.

FIG. 2 is a graph showing the thermogravimetric analysis (TG-DSC) chart of the crystal (crystal A) obtained in Comparative Example 1.

FIG. 3 shows the spatial arrangement of the single crystal derived from X-ray diffraction of the crystal (crystal A) obtained in Comparative Example 1.

FIG. 4 shows powder X-ray diffraction (XRD) of the crystal (crystal B) obtained in Example 1.

FIG. 5 is a graph showing the thermogravimetric analysis (TG-DSC) chart of the crystal (crystal B) obtained in Example 1.

FIG. 6 shows the spatial arrangement of the single crystal derived from X-ray diffraction of the crystal (crystal B) obtained in Example 1.

FIG. 7 is a graph showing the differential scanning calorimetry (DSC) chart of the epoxy resin compositions obtained in Example 3, and Comparative Examples 2 to 3.

FIG. 8 is a graph showing the differential scanning calorimetry (DSC) chart of the epoxy resin compositions obtained in Example 4, and Comparative Examples 4 to 5.

MODE OF CARRYING OUT THE INVENTION

The crystal polymorph of a clathrate compound consisting of TEP and 2P4MHZ (molar ratio of TEP:2P4MHZ is 1:2) of the present invention (hereinafter sometimes abbreviated to crystal B) is characterized by having peaks at diffraction angles (2θ) of 11.20°, 13.36°, 14.36°, 18.16°, 19.20°, 19.68°, 20.84°, 21.48°, 22.56°, 23.76° and 24.08° in Powder X-ray Diffraction.

Crystals each having a diffraction angle (2θ) within the range of ±0.2° are the same crystal as the crystal of the present invention.

The "clathrate compound" in the present invention can be said to form a structure that is connected by weak bonds such as hydrogen bond between hosts (TEP), where guest compounds (2P4MHZ) are trapped in the space of the structure. The clathrate compound in the present invention further refers to a compound encompassing salts.

The crystal polymorph of the present invention can be obtained, for example, by dissolving crystal A obtained by the method described in Patent Document 2, etc. in a solvent, followed by recrystallizing. Crystal A may be dissolved completely in a solvent, or the filtrate may be used after it is partially dissolved. Examples of solvents used for recrystallization can include, preferably, alcohols having 1 to 4 carbon atoms, and examples of such alcohols can specifically include methanol, ethanol, n-propanol, isopropanol, n-butanol, isobutanol, s-butanol, t-butanol, and among them methanol is preferred. The temperature for dissolving crystal A is not particularly limited and can be any temperature as long as it is within a range from room temperature to the boiling point of the solvent. The method of recrystallization is not particularly limited but can include, specifically, a method of heating to dissolve crystal A, followed by cooling, a method of dissolving crystal A in a solvent and gradually distilling off the solvent to deposit crystals, a method of adding a poor solvent for crystals to the solution, or a combination of these methods, etc., and among them a method of dissolving crystals and then gradually distilling off the solvent to less than or equal to its saturation concentration to deposit crystals is preferred.

Further, crystal B can be obtained by dissolving or suspending about 1 mole of TEP and about 2 moles of 2P4MHZ in a solvent, followed by crystallization. Examples of such solvents can include an alcohol having 1 to 4 carbon atoms, and examples of such alcohol can specifically include methanol, ethanol, n-propanol, isopropanol, n-butanol, isobutanol, s-butanol, t-butanol, and among them methanol is preferred. Crystallization may be performed after TEP and 2P4MHZ are completely dissolved, or crystallization may be performed after TEP and 2P4MHZ are partially dissolved and filtrated. The temperature for dissolving TEP and 2P4MHZ is not particularly limited and can be any temperature as long as it is within a range from room temperature to the boiling point of the solvent. The methods of crystallization are not particularly limited but can include, specifically, a method of heating to dissolve TEP and 2P4MHZ, followed by cooling, a method of dissolving TEP and 2P4MHZ in a solvent and gradually distilling off the solvent to deposit crystals, a method of adding a poor solvent for crystals to the solution, or a combination of these methods, etc., and among them a method of dissolving crystals and then gradually distilling off the solvent to less than or equal to its saturation concentration to deposit crystals is preferred.

The curable resin composition of the present invention is a composition containing an epoxy resin and crystal B as a curing agent or a curing accelerator.

For epoxy resins, it is preferable to use an epoxy resin having 2 or more epoxy groups in one molecule (hereinafter also referred to as "polyfunctional epoxy resin"). Here, epoxy resin refers to a prepolymer before curing and includes monomers and oligomers. Specifically, examples can include: novolac-type epoxy resin including phenol novolac-type epoxy resin and orthocresol novolac-type epoxy resin, that is obtained by epoxidizing an novolak resin wherein the novolak resin is obtained by condensing or co-condensing, in the presence of acidic catalyst, at least one phenolic compound selected from the group consisting of a phenol compound (such as phenol, cresol, xylenol, resorcin, catechol, bisphenol A, and bisphenol F) and a naphthol compound (such as α-naphthol, β-naphthol, and dihydroxynaphthalene), with aliphatic aldehyde compound such as formaldehyde, acetaldehyde, and propionaldehyde; triphenylmethane-type epoxy resin that is obtained by epoxidizing triphenylmethane-type phenol resin wherein the triphenylmethane-type phenol resin is obtained by condensing or co-condensing, in the presence of an acidic catalyst, the above-described phenolic compound with aromatic aldehyde compound such as benzaldehyde and salicylaldehyde; copolymerized type epoxy resin that is obtained by epoxidizing novolak resin wherein the novolak resin is obtained by co-condensing, in the presence of an acidic catalyst, the above-described phenol compound and naphthol compound with aldehyde compound; diphenylmethane-type epoxy resin which is a diglycidyl ether of bisphenol A, bisphenol F, etc.; biphenyl-type epoxy resin which is a diglycidyl ether of alkyl substituted or unsubstituted biphenol; stilbene-type epoxy resin which is a diglycidyl ether of stilbene-based phenol compound; sulfur atom-containing epoxy resin which is a diglycidyl ether of bisphenol S, etc.; epoxy resin which is a glycidyl ether of alcohols such as butanediol, polyethyleneglycol and polypropyleneglycol; glycidyl ester-type epoxy resin of polyvalent carboxylic acid compound such as phthalic acid, isophthalic acid and tetrahydrophthalic acid; glycidylamine-type epoxy resin which is obtained by substituting glycidyl group for the active hydrogen bonding to the nitrogen atom of aniline, diaminodiphenylmethane, isocyanuric acid, etc.; dicyclopentadiene-type epoxy resin which is obtained by epoxidizing the co-condensation resin of dicyclopentadiene and phenol compound; alicyclic-type epoxy resin which is obtained by epoxidizing the olefin bond in a molecule, such as vinylcyclohexene diepoxide, 3,4-epoxycyclohexylmethyl-3,4-epoxycyclohexane carboxylate, 2-(3,4-epoxy)cyclohexyl-5, 5-spiro(3,4-epoxy)cyclohexane-m-dioxane; glycidyl ether of paraxylylene modified phenol resin; glycidyl ether of metaxylylene modified phenol resin; glycidyl ether of terpene modified phenol resin; glycidyl ether of dicyclopentadiene modified phenol resin; glycidyl ether of cyclopentadiene modified phenol resin; glycidyl ether of polycyclic aromatic ring modified phenol resin; naphthalene-type epoxy resin that is a glycidyl ether of naphthalene ring-containing phenol resin; halogenated phenol novolac-type epoxy resin; hydroquinone-type epoxy resin; trimethylolpropane-type epoxy resin; linear aliphatic epoxy resin that is obtained by oxidizing the olefin bond with peroxy acid such as peroxy acid; diphenylmethane-type epoxy resin; aralkyl-type epoxy resin which is obtained by epoxidizing aralkyl-type phenol resin such as phenol aralkyl resin, and naphthol aralkyl resin. These can be used independently or in combination of two or three or more.

The mixing ratio of crystal B contained in the curable resin composition of the present invention is not limited as long as it is, in terms of 2P4MHZ contained in crystal, the same amount as the amount of 2P4MHZ that is normally contained in an epoxy resin composition is contained, specifically a range of 0.1 to 10 parts by weight with respect to 100 parts by weight of epoxy resin contained in the composition is preferred, and further a range of 1 to 5 parts by weight is preferred.

The curable resin composition of the present invention can be formulated as necessary with various additives such as other curing agents, other curing accelerators, plasticizer, organic solvent, reactive diluent, extender, filler, stiffener, pigment, flame retardant, thickener and release agent.

The curable resin composition of the present invention can be suitably used for the use of, for example, adhesive agent, semiconductor sealing material, printed circuit board laminate, varnish, powder paint, cast material, ink, fiber-reinforced composite material, etc.

The curable resin composition of the present invention can be obtained by directly mixing an epoxy resin, crystal B, and an additive which is formulated as necessary, or by mixing them in a solvent. The mixing may be conducted by heating at about 60 to 100° C. to form an adequate mixing state. The mixing means are not particularly limited but, for example, a sun-and-planet agitator, an extruder, a homogenizer, a mechanochemical agitator, a twin roll, Banbury mixer, etc. are suitably used.

Cured materials can be obtained by heat treating curable resin compositions and examples can include cured films obtained by painting or coating said composition on a base material. Heat treating can be performed at 50° C. to 250° C. for 15 minutes to 50 hours, preferably at 60° C. to 200° C. for 2 hours to 24 hours. Painting or coating of said composition can be performed by publicly known methods.

EXAMPLES

The present invention will be explained in detail referring to the examples in the following, but the present invention is not intended to be limited to the following examples.

[Analytical Method]
<Powder X-Ray Diffraction (XRD)>

Measurement was performed by loading crystals into a sample loading part of a glass test plate and using an powder X-ray diffraction system (Ultima IV, manufactured by Rigaku Corporation) under following conditions.
X-ray source: Cu, 40 kV-40 mA
Measurement method: convergence
Filter: Kβ filter
Scan speed: 5°/minute
<Single Crystal Structure X-Ray Diffraction>

(Crystal A) Single crystal X-ray diffraction intensity was measured by using an imaging plate single crystal X-ray structural analysis system (R-AXIS RAPID2, manufactured by Rigaku Corporation) with X-ray source CuKα ($\lambda$=1.541865 Å), at −180° C.

(Crystal B) Single crystal X-ray diffraction intensity was measured by using a CCD type single crystal X-ray diffraction system (CCD Mercury2, manufactured by Rigaku Corporation) with X-ray source SPring-8 synchrotron radiation ($\lambda$=0.699900 Å), at −188° C.
<Thermogravimetric Analysis (TG-DSC)>

Measurement was performed by using a thermogravimetric analysis system (product name: TGA-DSC1, manufactured by Mettler-Toledo International Inc.) and placing about 3 mg of crystals in an aluminum container, under nitrogen purging (nitrogen flow rate 50 mL/minute), with a rate of temperature increase of 20° C./minute and within a measurement temperature range from room temperature to 500° C.
<Differential Scanning Calorimetry (DSC)>

Measurement was performed by using a differential scanning calorimetry system (product name: DSC1, manufactured by Mettler-Toledo International Inc.) and placing about 8 mg of crystals in an aluminum container, under nitrogen purging (nitrogen flow rate 50 mL/minute), with a rate of temperature increase of 10° C./minute and within a measurement temperature range from 30° C. to 350° C.

Comparative Example 1

A clathrate compound of TEP and 2P4MHZ was prepared according to the method described in Patent Document 2 and the crystal (crystal A) of the clathrate compound was obtained. The results from powder X-ray diffraction analysis (XRD) and thermogravimetric analysis (TG-DSC) of the obtained crystal are shown in FIG. 1 and FIG. 2. From the result of XRD in FIG. 1, the crystal was a crystal polymorph (crystal A) having characteristic diffraction peaks at diffraction angles (2θ): 8.12°, 10.12°, 12.72°, 13.68°, 14.60° and 20.24°. Further, the endothermic peak was confirmed at around 222° C. from the result of TG-DSC in FIG. 2.

Table 1 shows the crystal data from X-ray diffraction of the single crystal obtained in Comparative Example 1, and FIG. 3 shows the spatial arrangement of the single crystal obtained in Comparative Example 1.

TABLE 1

| | |
|---|---|
| Identification code | shelx |
| Empirical formula | $C_{48}H_{46}N_4O_6$ |
| Formula weight | 774.89 |
| Temperature | 93(2) K |
| Wavelength | 1.54186 Å |
| Crystal system | monoclinic system |
| Space group | P21/c |

TABLE 1-continued

| | |
|---|---|
| Unit cell dimension | a = 8.39300(15) Å α = 90° |
| | b = 17.4082(3) Å β = 103.1613(8)° |
| | c = 14.1948(3) Å γ = 90°. |
| Volume | 2019.48(6) Å$^3$ |
| Z-score | 2 |
| Density (calculated value) | 1.274 Mg/m$^3$ |
| Absorbing coefficient | 0.680 mm$^{-1}$ |
| F(000) | 820 |
| Crystal size | 0.160 × 0.156 × 0.100 mm$^3$ |
| θ range for data collection | 4.084 to 68.246°. |
| Range of factors | −10 <= h <= 9, −20 <= k <= 20, −17 <= l <= 16 |
| number of collected reflections | 23062 |
| number of independent reflections | 3693 [R(int) = 0.0433] |
| Integrity for θ = 67.686° | 100.0% |
| Absorption correction | empirical equivalence |
| Max and min transmission rate | 0.935 and 0.764 |
| Refinement method | full matrix least squares method of F$^2$ |
| Data/Constraint/Parameter | 3693/4/295 |
| Fitting of F$^2$ | 1.098 |
| Final R-factor [I > 2sigma(I)] | R$_1$ = 0.0594, wR$_2$ = 0.1736 |
| R-factor (whole data) | R$_1$ = 0.0753, wR$_2$ = 0.1854 |
| Attenuation coefficient | n/a |
| Max diffraction peak and hole | 0.402 and −0.234 e · Å$^{-3}$ |

Example 1

Crystals of the clathrate compound obtained in Comparative Example 1 and methanol were put into a three-necked flask and the crystals were completely dissolved. A crystal of a clathrate compound with a clathrate ratio (TEP:2P4MHZ) =1:2 (crystal B) was obtained by leaving to stand as is with the top opened at room temperature, slowly evaporating methanol, depositing the crystal, and filtrating.

The results of powder X-ray diffraction analysis (XRD) and thermogravimetric analysis (TG-DSC) of the obtained crystal are shown in FIG. 4 and FIG. 5. From the result of XRD in FIG. 4, the crystal was found to be a crystal polymorph having characteristic diffraction peaks at diffraction angles (2θ): 11.20°, 13.36°, 14.36°, 18.16°, 19.20°, 19.68°, 20.84°, 21.48°, 22.56°, 23.76° and 24.08°, which is distinct from the crystal of Comparative Example 1. Further, the endothermic peak was confirmed at around 230° C. from the result of TG-DSC in FIG. 5.

X-ray diffraction was measured with respect to the single crystal obtained in the above and its spatial arrangement was identified. The obtained crystal data is shown in Table 2 and the spatial arrangement of the crystal, plotted from the obtained crystal data, is shown in FIG. 6.

TABLE 2

| | |
|---|---|
| Identification code | shelx |
| Empirical formula | C$_{48}$H$_{46}$N$_4$O$_6$ |
| Formula weight | 774.89 |
| Temperature | 85(2) K |
| Wavelength | 0.6999 Å |
| Crystal system | monoclinic system |
| Space group | P2$_1$/c |
| Unit cell dimension | a = 8.285(2) Å α = 90° |
| | b = 16.280(4) Å β = 110.243(12)° |
| | c = 15.134(4) Å γ = 90° |
| Volume | 1915.2(8) Å$^3$ |
| Z-score | 2 |
| Density (calculated value) | 1.344 Mg/m$^3$ |
| Absorbing coefficient | 0.086 mm$^{-1}$ |
| F(000) | 820 |
| Crystal size | 0.054 × 0.045 × 0.009 mm$^3$ |
| θ range for data collection | 1.874 to 24.935°. |
| Range of factors | −9 <= h <= 9, −19 <= k <= 19, −18 <= l <= 18 |
| number of collected reflections | 15705 |
| number of independent reflections | 3495 [R(int) = 0.1201] |
| Integrity for θ = 67.686° | 100.0% |
| Absorption correction | empirical equivalence |
| Max and min transmission rate | 0.999 and 0.369 |
| Refinement method | full matrix least squares method of F$^2$ |
| Data/Constraint/Parameter | 3495/3/275 |
| Fitting of F$^2$ | 0.974 |
| Final R-factor [I > 2 sigma(I)] | R$_1$ = 0.0526, wR$_2$ = 0.1107 |
| R-factor (whole data) | R$_1$ = 0.0907, wR$_2$ = 0.1283 |
| Attenuation coefficient | n/a |
| Max diffraction peak and hole | 0.224 and −0.261 e · Å$^{-3}$ |

Example 2

Into a flask, 2.94 g (73.7 mmol) of TEP, 2.78 g (147.5 mmol) of 2P4MHZ, and methanol were added and TEP and 2P4MHZ were dissolved completely in a solvent. A crystal of a clathrate compound with a clathrate ratio (TEP: 2P4MHZ)=1:2 (crystal B) was obtained by leaving to stand as is with the top opened at room temperature, slowly evaporating methanol, depositing the crystal, and filtrating.

The results of powder X-ray diffraction analysis (XRD) and thermogravimetric analysis (TG-DSC) of the obtained crystal were the same as that of Example 1.

Example 3 to Example 4 and Comparative Example 2 to Comparative Example 5

Epoxy resin composition was obtained by mixing an epoxy resin with a curing agent with a mixing ratio shown in Table 3 such that the curing agent becomes 4 phr with respect to the epoxy resin in 2P4MHZ equivalent. These compositions were preserved at 40° C. and the preservation stability was evaluated by counting the days until the curing was visually confirmed. The results are shown in Table 4.

TABLE 3

| Composition | | Example 3 | Comparative Example 2 | Comparative Example3 | Example 4 | Comparative Example 4 | Comparative Example 5 |
|---|---|---|---|---|---|---|---|
| Epoxy resin A(*1)(g) | | 2.5 | 2.5 | 2.5 | | | |
| Epoxy resin B(*2)(g) | | | | | 2.5 | 2.5 | 2.5 |
| Curing | 2P4MHZ(g) | | 0.1 | | | 0.1 | |
| Agent | Crystal A(g) | | | 0.2 | | | 0.2 |
| | Crystal B(g) | 0.2 | | | 0.2 | | |

(*1)bisphenol A type epoxy resin (product name: Epotohto YD-128, NIPPON STEEL & SUMIKIN CHEMICAL CO., LTD; Epoxy equivalent 184-194 g/eq)
(*2)N,N,N',N'-tetraglycidyl diaminodiphenylmethane (TGDDM)

Further, the differential scanning calorimetry (DSC) was performed on the composition. From the results, the obtained cure initiation temperature and the peak temperature of the heat of the reaction are shown in Table 4 and DSC charts of Examples are shown in FIG. 7 and FIG. 8, respectively.

TABLE 4

| | | Example 3 | Comparative Example 2 | Comparative Example 3 | Example 4 | Comparative Example4 | Comparative Example5 |
|---|---|---|---|---|---|---|---|
| | Days to cure | no curing in 37 days | curing in 6-9 days | curing in 3-5 days | no curing in 46 days | curing in 11-15 days | curing in 15-21 days |
| DSC | Cure initiation temperature (° C.) | 161.8 | 153.58 | 159.3 | 163.8 | 160.5 | 159.3 |
| | Peak temperature of heat reaction (° C.) | 167.8 | 157.06 | 163.3 | 168.8 | 163.6 | 163.3 |

From the results of Table 4, it has been revealed that when a clathrate compound of crystal B is used, the preservation stability of its epoxy resin compositions was significantly improved as compared to when using a clathrate compound of crystal A or 2P4MHZ. Further, it was found that the function as a clathrate compound is stably exerted regardless of epoxy resins.

Further, from the result of DSC in Table 4, it has been revealed that when a clathrate compound of crystal B was used as a curing agent, the cure initiation temperature and the peak temperature of the heat of reaction of its epoxy resins were found to shift to a high temperature side as compared to when using a clathrate compound of crystal A or 2P4MHZ as a curing agent.

The invention claimed is:

1. A crystal polymorph of a clathrate compound consisting of 1,1,2,2-tetrakis(4-hydroxyphenyl)ethane and 2-phenyl-4-methyl-5-hydroxymethylimidazole, wherein:
   a molar ratio of 1,1,2,2-tetrakis(4-hydroxyphenyl)ethane to 2-phenyl-4-methyl-5-hydroxymethylimidazole is 1:2, and
   the crystal polymorph has diffraction peaks at diffraction angles (2θ) of 11.20°, 13.36°, 14.36°, 18.16°, 19.20°, 19.68°, 20.84°, 21.48°, 22.56°, 23.76%, and 24.08° in a powder X-ray diffraction pattern as measured using a CuKα ray.

2. A method of producing the crystal polymorph according to claim 1, comprising a step of recrystallizing a crystal of a clathrate compound consisting of 1,1,2,2-tetrakis(4-hydroxyphenyl)ethane and 2-phenyl-4-methyl-5-hydroxymethylimidazole, wherein the crystal has diffraction peaks at diffraction angles (2θ) of 8.12°, 10.12°, 12.72°, 13.68°, 14.60° and 20.24° in a powder X-ray diffraction pattern as measured using a CuKα ray.

3. A method of producing the crystal polymorph according to claim 1, comprising a step of crystallizing a clathrate compound consisting of 1,1,2,2-tetrakis(4-hydroxyphenyl)ethane and 2-phenyl-4-methyl-5-hydroxymethylimidazole from an alcohol solution or suspension containing 1,1,2,2-tetrakis(4-hydroxyphenyl)ethane and 2-phenyl-4-methyl-5-hydroxymethylimidazole.

4. A curing agent for epoxy resins or a curing accelerator for epoxy resins, containing the crystal polymorph according to claim 1.

5. A curable resin composition containing an epoxy resin and the curing agent for epoxy resins or the curing accelerator for epoxy resins according to claim 4, or a cured product thereof.

* * * * *